United States Patent [19]

Ribaldone et al.

[11] 4,077,966
[45] Mar. 7, 1978

[54] METHOD FOR THE PREPARATION OF THE MONOPOTASSIUM SALT OF 1,2,5-THIADIAZOL-3,4-DICARBOXYLIC ACID, AND INTERMEDIATE PRODUCT

[75] Inventors: Giuseppe Ribaldone, Gallarate (Varese); Renato Grecu, Cameri (Novara), both of Italy

[73] Assignee: Montedison S.p.A., Milan, Italy

[21] Appl. No.: 775,767

[22] Filed: Mar. 9, 1977

[30] Foreign Application Priority Data

Mar. 17, 1976  Italy ............................. 21289 A/76

[51] Int. Cl.² .......................................... C07D 285/10
[52] U.S. Cl. ................................................ 260/302 D
[58] Field of Search .................................... 260/302 D

[56] References Cited
FOREIGN PATENT DOCUMENTS 928,571  6/1963  United Kingdom ............ 260/302 D Primary Examiner—R. Gallagher
Attorney, Agent, or Firm—Hubbell, Cohen, Stiefel & Gross

[57] ABSTRACT

Process for the preparation of the monopotassium salt of 1,2,5-thiadiazol-3,4-dicarboxylic acid (I). Involves double-stage saponification of 3,4-dicyano-1,2,5-thiadiazole (II), 3-cyano-4-carbamoyl-1,2,5-thiadiazole (III) is obtained from an aqueous suspension of 3,4-dicyano-1,2,5-thiadiazole (II) by catalytic hydration through the addition of aqueous KOH, desirably at a temperature of from 20° to 50° C. and with a molar ratio of 3,4-dicyano-1,25-thiadiazole (II) to KOH of from 1:0.01 to 1:0.8. This is followed by hydrolysis, by the further addition of aqueous KOH, desirably at a temperature of from 85° to 100° C., until attaining an overall molar ratio of 3,4-dicyano-1,2,5-thiadiazole (II) to KOH of from about 1:2.0 to 1:2.35, a molar ratio of 3,4-dicyano-1,2,5-thiadiazole (II) to $H_2O$ of from about 1:20 to 1:23. Thereafter, from the resulting solution of dipotassium salt of 1,2,5-thiadiazole-3,4-diccarboxylic acid, the monopotassium salt is separated by acidification of said solution.

10 Claims, No Drawings

METHOD FOR THE PREPARATION OF THE MONOPOTASSIUM SALT OF 1,2,5-THIADIAZOL-3,4-DICARBOXYLIC ACID, AND INTERMEDIATE PRODUCT

CROSS-REFERENCE TO RELATED APPLICATIONS

This application is related to and incorporates by reference the contents of copending application Ser. No. 733,940, filed Oct. 19, 1976, and entitled "Process For Preparing 3,4-Dicyano-1,2,5-Thiadiazole", and which is owned by the unrecorded assignee hereof.

BACKGROUND OF THE INVENTION

1. Field of the Invention

The present invention relates to a method for the preparation of the monopotassium salt of 1,2,5-thiadiazole-3,4-dicarboxylic acid. More particularly, it relates to a method for the preparation of the monopotassium salt of 1,2,5-thiadiazole-3,4-dicarboxylic acid of the following formula:

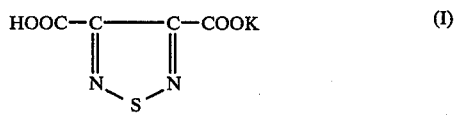

starting from 3,4-dicyano-1,2,5-thiadiazole, a readily obtainable compound, for instance, by cyclization of diaminomaleonitrile (a tetramer of hydrocyanic acid) with S-chlorides, according to methods known in the art.

2. Description of the Prior Art

The monopotassium salt of 1,2,5-thiadiazole-3,4-dicarboxylic acid is a known compound which has important and useful applications as an intermediate for the preparation of polyamide polymers for use as effective membranes for reverse osmosis, which membranes are used in the field of sea water desalination. As is well known, said polymers may be obtained, for instance, by the interfacial polymerization of diamines with the dichloride derivative of 1,2,5-thiadiazol-3,4-dicarboxylic acid, which in turn is obtainable by effecting chlorination (with $SOCl_2$) of the monopotassium salt of 1,2,5-thiadiazol-3,4-dicarboxylic acid, which salt may be obtained according to the method of this invention.

Prior methods for preparing the monopotassium salt of 1,2,5-thiadiazol-3,4-dicarboxylic acid are based on the oxidation of 2,1,3-benzo-thiadiazoles with potassium permanganate. Such methods are, however, unsuitable for industrial use because of the low yields encountered as well as the complexities of operation.

It is also known to prepare the monopotassium salt of the 1,2,5-thiadiazol-3,4-dicarboxylic acid by saponification of 3,4-dicyano-1,2,5-thiadiazole with KOH, according to the known technique of alkaline saponification of nitriles. This method involves the heating, under reflux, of a suspension of the nitrile in dilute aqueous KOH, with a high excess of KOH over the stoichiometric quantity required. We have found, however, that in utilizing this saponification technique with respect to 3,4-dicyano-1,2,5-thiadiazole, the yields do not exceed 85%, and in addition, there occurs the undesirable formation of cyanide ions due to a secondary reaction of the KOH with the 3,4-dicyano-1,2,5-thiadiazole. Moreover, the reaction volume is considerable, so that in order to isolate the reaction product, which exhibits a fair solubility in water, one must resort to considerable concentration of the solution at the end of the reaction.

In addition to the above drawbacks, there is also the fact that there is present in the waste waters considerable quantities of cyanides, with consequent potential damages and environmental problems.

SUMMARY OF THE INVENTION

The present invention provides an industrially feasible process for the preparation of the monopotassium salt of 1,2,5-thiadiazol-3,4-dicarboxylic acid in high yields, while reducing to a minimum the formation of cyanide ions, and this process may be practiced with small reaction volumes.

According to this invention the monopotassium salt of 1,2,5-thiadiazol-3,4-dicarboxylic acid [formula (I)] is prepared by a two stage saponification of 3,4-dicyano-1,2,5-thiadiazole (II). To that end, 3-cyano-4-carbamoyl-1,2,5-thiadiazole (III) is obtained from an aqueous suspension of 3,4-dicyano-1,2,5-thiadiazole (II) by hydration with the addition of aqueous KOH at a temperature of from about 20° to 50° C., with the molar ratio of 3,4-dicyano-1,2,5-thiadiazole (II) to KOH being from about 1:0.01 to 1:0.8. This is followed by the further addition of aqueous KOH at a temperature of from about 85° to 100° C. until one has obtained an overall molar ratio, as between 3,4-dicyano-1,2,5-thiadiazole (II) and KOH of from about 1:2.0 to 1:2.35, and an overall molar ratio, as between 3,4-dicyano-1,2,5-thiadiazole (II) and $H_2O$ of from about 1:20 to 1:23. Finally, according to conventional techniques, the monopotassium salt (I) is separated by acidification of the solution of the dipotassium salt (IV) of 1,2,5-thiadiazol-3,4-dicarboxyl acid.

The intermediate reaction product, 3-cyano-4-carbamoyl-1,2,5-thiadiazole (III), obtained in the first stage, is itself a new compound.

From the thus obtained solution of the dipotassium salt (IV), the monopotassium salt (I) of 1,2,5-thiadiazol-3,4-dicarboxylic acid is then precipitated by acidification up to a pH of from about 2 to 3, as by the addition of hydrochloric acid or any other strong inorganic acid, according to conventional techniques.

DESCRIPTION OF THE PREFERRED EMBODIMENTS

The reaction sequence of the present invention may be schematically represented as follows:

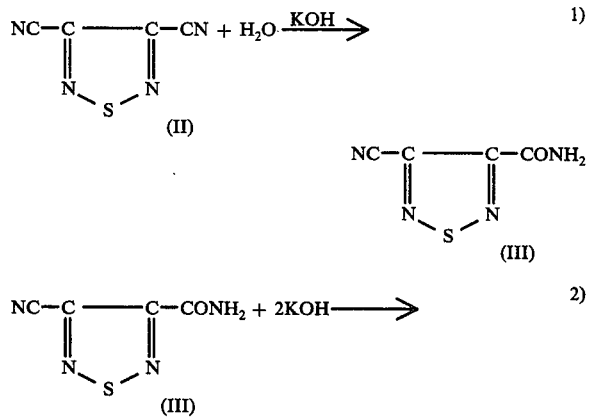

-continued

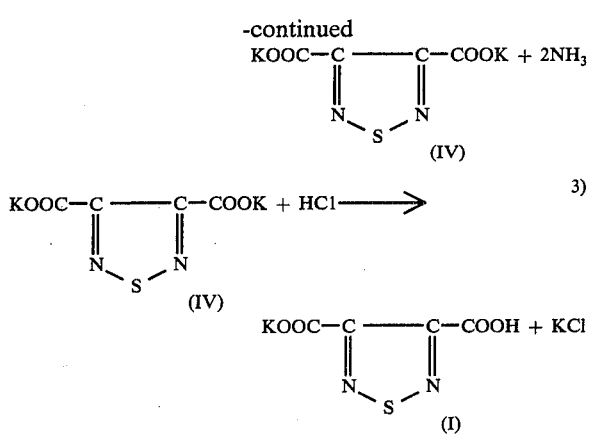

In the present invention, the use of commercial solutions of KOH, wherein the concentration is of the order of 38–40% by weight, is particularly advantageous. Thus, a commercial KOH solution may be used directly, without any further dilution in water.

The sequential order in which the reactants are introduced, as well as the quantities of KOH and $H_2O$ and the temperature of the first stage, are critical parameters for the correct course of the reaction.

In order to start the reaction it is necessary that the KOH solution be added to the aqueous suspension of 3,4-dicyano-1,2,5-thiadiazole (II). If, instead one uses the reverse sequence, adding the dinitrile (II) to the KOH solution, one obtains an undesirable increase in cyanide ions due to a degradation reaction of the dinitrile (II) by the KOH.

For the first stage of the reaction there is used from about 0.01 to 0.8 mole of KOH, and preferably from about 0.02 to 0.7 mole, per mole of dinitrile (II). Greater quantities give no advantages, inasmuch as the KOH during this first stage does not participate as a true reactant, as is evident from reaction 1), but only as a hydration catalyst. Indeed, greater quantities may make the first stage reaction less selective. The KOH is fed in the form of a solution, preferably as a commercial (38–40% by weight) solution.

The quantity of water necessary for suspending the 3,4-dicyano-1,2,5-thiadiazole (II) in the first stage is desirably about 10 moles/mole of dinitrile (II). Such a quantity is sufficient for ensuring good stirrability of the suspension. Greater quantities do not result in any practical advantage and moreover, in the following stage would require the use of KOH solutions having a concentration greater than 38–40%, a concentration difficult to obtain on the market, in order to attain the final values of the given molar ratios of the second stage.

However, if desired, one can of course separately prepare and then use solutions that are more concentrated than 38–40%, as by dissolving solid KOH in water.

Since the hydration reaction of the dinitrile (II) of the first stage is strongly exothermic, it is necessary that the temperature be maintained, by cooling, at about 20°–50° C, so as to prevent the reaction from taking an uncontrollable course, which would lead to decomposition of the dinitrile (II) and to an increase of cyanide ions.

Under such temperature conditions (20° to 50° C.), the hydration reaction will continue for approximately 30 to 60 minutes.

If desired, by operating within a temperature range of about 20° to 35° C, or when the reaction mixture obtained when operating at about 35° to 50° C is cooled down to 20° to 35° C., there is obtained a heterogeneous mixture containing the 3-cyano-4-carbamoyl-1,2,5-thiadiazole (III) in suspension, and it may then be readily separated by filtering. This operation, however, is not necessary for the practice of this process, inasmuch as the solution or suspension of the cyanoamide (III) may be used directly in the subsequent hydrolysis stage. The process may thus be carried out in a continuous manner, or in a batch operation after separating the cyanoamide (III).

The second stage of the process is carried out by feeding to the solution or suspension of cyanoamide (III) an aqueous solution of KOH, preferably at a concentration of 38 to 40%, or higher if in the first stage there was used, for the suspension of the dinitrile (II), a quantity of water greater than 10 moles/mole of dinitrile.

Of course, the quantity of aqueous KOH to be fed into the second stage will depend upon the quantities of KOH and $H_2O$ previously introduced into the first stage, since, as previously pointed out, according to the process, there should be attained a total, or overall molar ratio of from 2.0 to 2.35 moles of KOH per mole of dintrile (II) and from 20 to 23 moles of $H_2O$ per mole of dinitrile (II).

Preferably one operates with the following molar ratios:

Dinitrile (II)/KOH/$H_2O$ = 1/2.15–2.30/21–22.

Thus, the quantities of KOH and $H_2O$ to be fed into the second stage are easily determined by subtracting from the above mentioned overall values the corresponding quantities introduced into the first stage.

For example, if in the first stage there were used about 10 moles of $H_2O$ for suspending one mole of dinitrile (II), and if one wishes to feed, overall, 2.15–2.30 moles of KOH in the form of a 38% solution, the total water introduced into reaction at the end of the second stage, where the KOH has a 38% concentration, will automatically amount to 21–22 moles.

Quantities of KOH greater than 2.35 moles per mole of dinitrile (II) do not give any practical advantage. Rather, they would represent a waste, even as regards the acidifying agent, which would subsequently have to be used in quantities that were proportionately higher. Moreover, there would be greater reaction volumes involved and an increase in the quantity of inorganic salts that would precipitate with the monopotassium salt of the 1,2,5-thiadiazol-3,4-dicarboxylic acid (I).

As far as the total quantity of water used in the process, it appears to represent the optimum quantity with respect to obtainable yields, the reaction volumes, and the stirrability of the reaction mixture.

The reaction temperature of the second stage should be from about 85° to 100° C, and preferably from about 90° to 95° C. When operating at these temperatures the duration of the hydrolysis reaction will be from about 1.5 to 3 hours. Overall, the saponification process will ordinarily have a maximum duration of about 4 hours.

At the end of the reaction one will obtain a solution of the potassium salt (IV) of 1,2,5-thiadiazol-3,4-dicarboxylic acid, from which, by acidification to a pH of from about 2 to 3, there will precipitate the monopotassium salt (I), in a yield exceeding 95%. As acidifying agents there desirably may be used strong inorganic acids, such as, e.g., HCl, $HNO_3$, or $H_2SO_4$. Preferably a concentrated aqueous solution of hydrochloric acid is employed.

The product thus obtained contains about 10% potassium chloride as impurity. The raw product is usable as such, without any sort of purification, by reaction with $SOCl_2$ so as to thereby be converted to the dichloride of 1,2,5-thiadiazol-3,4-dicarboxylic acid, which is used as an intermediate for the polymerization with diamines so as to obtain polymers for use in reverse-osmosis membranes.

The present process is not only applicable to pure 3,4-dicyano-1,2,5-thiadiazole (II), but also to the raw product as obtained, for instance, as described in our previously referred to application Ser. No. 733,940, which relates to the preparation of the raw products by cyclization of diamino-maleonitrile with thionyl chloride. Such a process leads to a reaction product comprising raw 3,4-dicyano-1,2,5-thiadiazole (II) which, without any further purification, may be converted directly into a monopotassium salt of the 1,2,5-thiadiazol-3,4-dicarboxylic acid (I), according to the method of this invention.

The process of this invention may desirably be carried out in the following manner.

First, one mole of solid 3,4-dicyano-1,2,5-thiadiazole (II) is suspended in a quantity of water sufficient to obtain an easily stirrable mixture. Then, under stirring, there are admixed from 0.01 to 0.8 mole of KOH in the form of an aqueous solution. There occurs an exothermic reaction which is controlled by cooling so as to maintain a temperature of about 20° to 50° C. At this stage the 3,4-dicyano-1,2,5-thiadizole (II) passes into solution, hydrating to form 3-cyano-4-carbamoyl-1,2,5-thiadiazole (III), which may be separated as a solid if one operates at 20° to 35° C, or which will remain in solution if one operates at higher temperatures up to 50° C. This ends the first stage of the reaction.

To the solution or suspension, depending on the temperature used, of 3-cyano-4-carbamoyl-1,2,5-thiadiazole (III) thus obtained, is added (second stage) an aqueous solution of KOH in such a quantity as to obtain an overall solution containing 2.0 to 2.35 moles of KOH and 20 to 23 moles of $H_2O$, values which have been correlated to those of the first stage, with respect to one mol of 3,4-dicyano-1,2,5-thiadiazole (II) initially introduced into the reaction.

Thereafter the reaction mass is heated to about 85° to 100° C, until the evolution of ammonia completely ceases.

The solution obtained in this second stage is cooled to room temperature and then acidified to a pH of about 2 to 3, as by adding hydrochloric acid, nitric acid or sulfuric acid. There is thus formed a precipitate of the monopotassium salt of 1,2,5-thiadiazol-3,4-dicarboxylic acid (I), which precipitate is separated by filtering or centrifuging, and finally dried.

The process, as a result of the selective reaction conditions employed, ensures the obtention of high yields and a high purity of the product. Other advantages will be apparent from the subsequent examples.

In the following illustrative examples, there is given a further description of the present invention. Such description also includes an example (Example 4) covering the conversion of the monopotassium salt to the dichloride of 1,2,5-thiadiazol-3,4-dicarboxylic acid, which is a polymerization intermediate, as well as the use of raw 3,4-dicyano-1,2,5-thiadiazole (II) obtained by operating according to application Ser. No. 733,940.

There is also reported a comparative example (Example 6) carried out according to the known prior art technique, and a further comparative example (Example 5) demonstrating that the sequential order of the feeding in of the reactants in the first stage is a critical aspect of the invention.

EXAMPLE 1

Into a 750 ml glass reactor provided with a water bath, a thermometer, a stirrer, a reflux coolant and a funnel with tap, there were introduced:

136.13 g (1.0 mole) of 3,4-dicyano-1,2,5-thiadiazole;
186 ml (10.3 moles) of water.

Into the feeding funnel were loaded 340 g of a KOH solution at a concentration of 38% by weight (consisting of 2.3 moles of KOH and 11.7 moles of $H_2O$). Then, under stirring, 85 g of the KOH solution, corresponding to 0.575 mole of KOH and 2.920 moles of $H_2O$, were slowly introduced, while maintaining the temperature stabilized at between 45° and 50° C. by cooling.

After about 30 minutes following the adding of the KOH solution, the reaction was no longer exothermic and the reaction mixture, which originally had been heterogeneous, had become a solution.

Thereafter, the remaining 255 g of KOH solution (corresponding to 1.725 moles of KOH and 8.780 moles of $H_2O$) were rapidly introduced and the entire mixture was heated to 90° C. and maintained at this temperature for about 2 hours. After this period the evolution of ammonia had completely stopped. The thus obtained solution was cooled to room temperature and then acidified by the addition of a solution of concentrated hydrochloric acid until a pH of 2 had been reached. The reaction mass was then stirred at 15° to 20° C. for 30 minutes and the precipitate was then filtered and dried under vacuum in an oven at 100° C. until a constant weight had been reached.

There were obtained 231.7 g of the monopotassium salt of 1,2,5-thiadiazol-3,4-dicarboxylic acid (I), which appeared as a light yellow solid with a titer of 90%, the impurity being potassium chloride.

The yield, based on 3,4-dicyano-1,2,5-thiadiazole (II), was 98%. The product, crystallized from water, melted at 293° C. and gave an IR spectrum that was equal to that for an authentic comparative sample of the monopotassium salt of 1,2,5-thiadiazol-3,4-dicarboxylic acid (I).

The content of the saponification solution in $CN^-$ ions, referred to a mole of 3,4-dicyano-1,2,5-thiadiazole put into reaction, was $3.24 \times 10^{-3}$ moles.

EXAMPLE 2

Into the apparatus described in Example 1, there were introduced:

136.13 g (1.0 mole) of 3,4-dicyano-1,2,5-thiadiazole;
181 ml (10.0 moles) of water.

To the thus obtained suspension, while under stirring, there were added 3.0 g of a KOH solution at a concentration of 38% by weight (corresponding to 0.02 mole of KOH and 0.1 mole of $H_2O$).

This resulted in an exothermic reaction which was controlled by maintaining the temperature at between 20° and 25° C. by cooling. After about 30 minutes, the dinitrile (II) hydration reaction was accomplished and the suspension had been converted into a pasty mixture. This pasty mixture was then stirred for a further 30 minutes at room temperature and thereafter was filtered and the resulting solid was washed with a small amount of cold water.

After drying under vacuum until a constant weight was reached, there were obtained 146.0 g of 3-cyano-4-carbamoyl-1,2,5-thiadiazole (III), having a m.p. of 149° to 150° C.

After cyrstallization from water, there were obtained 128.6 g of pure product that had a m.p. of 150° to 151° C. The elemental analysis, infra-red (IR) spectrum, and mass spectrum were in perfect agreement with structural formula:

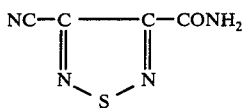
(III)

which is the reaction intermediate (III) obtained in the first stage of the present process.

This example shows that in the first stage of the process of this invention, 3-cyano-4-carbamoyl-1,2,5-thiadiazole (III) is formed by hydration of 3,4-dicyano-1,2,5-thiadiazole (II) using only catalytic amounts of aqueous KOH.

EXAMPLE 3

Into the apparatus described in Example 1 there were introduced:

136.13 g (1.0 mole) of 3,4-dicyano-1,2,5-thiadiazole;
181 ml (10.0 moles) of water.

Thereafter, into the feeding funnel were added 318 g of a solution of KOH at a concentration of 38% by weight (consisting of 2.15 moles of KOH and 1.0 mole of $H_2O$). Then, under stirring, 3.0 g of the KOH solution (corresponding to 0.22 mole of KOH and 0.1 mole of $H_2O$) were introduced. There resulted an exothermic reaction which was controlled by maintaining the temperature between 20° and 25° C. by cooling. After about 30 minutes the dinitrile (II) hydration reaction had been completed and the suspension had been transformed into a pasty mixture. Thereafter there was rapidly introduced the remaining KOH solution, 315 g (corresponding to 2.13 moles of KOH and 10.9 moles of $H_2O$), and the entire reaction mass was heated for 1.5 hours at 90° to 95° C.

The thus obtained solution was then treated according to the procedures of Example 1, thereby obtaining 228.2 g of the monopotassium salt of 1,2,5-thiadiazol-3,4-dicarboxylic acid (I) with a titer of 91%, the impurity being potassium chloride.

The yield, based on 3,4-dicyano-1,2,5-thiadiazole (II), was 97.8%.

The product, crystallized from water, showed chemical-physical characteristics identical with those of the product obtained in Example 1.

EXAMPLE 4

Into a glass reactor, provided with a hot water heating bath, a funnel with tap, a thermometer, a stirrer, a reflux cooler kept at −15° C. connected at the top with a valve containing $H_2SO_4$ for the control of the flow of the gas, there were introduced:

108.1 g of diaminomaleonitrile (1 mole)
357 g of $SOCl_2$ (3 moles).

The thus obtained mixture was heated under stirring to 50° C. and held at that temperature for about 4 hours, and then at 75° C. for 2 hours. Thereafter there was no further evolution of HCl and $SO_2$. From the thus obtained solution the excess thionyl chloride was distilled off under reduced pressure. To the resulting residue, which was raw 3,4-dicyano-1,2,5-thiadiazole, there were added 186 ml (10.3 moles) of water. The reaction mass was then heated at 40° to 45° C. until complete homogenization occurred. Then into the feeding funnel were added 340 g of a KOH solution at a concentration of 38% by weight (consisting of 2.3 moles of KOH and 11.7 moles of $H_2O$) and, in accordance with Example 1, there were fed in 85 g of this solution. An exothermic reaction occurred, and it was controlled by maintaining the temperature at 50° C. by cooling. About 30 minutes after the addition of the KOH solution, the reaction was no longer exothermic. The remaining KOH solution (255 g) was rapidly introduced and then the whole was heated at 90° C. for 2 hours.

The thus obtained solution was left to cool at room temperature and was then acidified with a solution of concentrated hydrochloric acid until a pH of 2.5 was reached. The solution was then stirred for a further 30 minutes, after which the precipitate was filtered and dried under vacuum in an oven at 100° C. until reaching a constant weight.

There were thus obtained 221.6 g of the monopotassium salt of 1,2,5-thiadiazol-3,4-dicarboxylic acid (I), with a titer of 90%, the impurity being potassium chloride. The yield based on the diaminomaleonitrile, amounted to 93%.

Then, according to the known technique, 100 g of the monopotassium salt of 1,2,5-thiadiazol-3,4-dicarboxylic acid (I) as obtained above, were suspended in 760 ml thionyl chloride, to which were then added 5 ml of dimethylformamide. The suspension was then reflux-heated for about 5 hours. The reaction mass was then cooled to room temperature and the insoluble salts were filtered. The filtrate was then subjected to fractional distillation, first at atmospheric pressure in order to recover the excess thionyl chloride, then under vacuum, collecting that fraction with a boiling point equal to 75° to 77° C./0.5 mm Hg.

Under cooling the distillate gave a solid mass of 86.9 g, which was the dichloride of 1,2,5-thiadiazol-3,4-dicarboxylic acid.

The IR spectrum of the thus obtained product was identical to that of a proven comparative sample of the dichloride of 1,2,5-thiadiazol-3,4-dicarboxylic acid. This product was suitable for subsequent use as the intermediate for the preparation of reverse osmosis membranes.

EXAMPLE 5

Comparative Example

In this example there was utilized a reverse feeding sequence with respect to the 3,4-dicyano-1,2,5-thiadiazole and the KOH solution.

The same equipment was used as described in Example 1. Into the feeding funnel were added 340 g of a KOH solution at a concentration of 38% by weight (consisting of 2.3 moles of KOH and 11.7 moles of $H_2O$), and then into the reactor were fed 85 g of this solution and 186 ml of water. Keeping the temperature at 45° to 50° C., under stirring, there were added over a period of about 30 minutes 136.13 g (1.0 mole) of 3,4- dicyano-1,2,5-thiadiazole (II). To the thus obtained solution were rapidly added the remaining 255 g of KOH solution (38% concentration), and the whole was then heated to 90° C. and maintained at that temperature for about 2 hours.

After this period of time, the evolution of ammonia had completely ceased. The thus obtained solution, after cooling to room temperature, was acidified with a solution of concentrated hydrochloric acid, until attaining a pH of 2. The solution was then stirred for 30 minutes at 15° to 20° C. and the precipitate was then filtered and dried under vacuum in an oven at 100° C., until a constant weight was attained.

There were thus obtained 214.6 g of the monopotassium salt of 1,2,5-thiadiazol-3,4-dicarboxylic acid (I), having a titer of 89.5%.

The yield, based on the 3,4-dicyano-1,2,5-thiadiazole (II) amounted to 90.5%.

The content of $CN^-$ ions in the saponification solution, per mole of reacted 3,4-dicyano-1,2,5-thiadiazole was $15.1 \times 10^{-3}$ moles. This example shows that, if the order of feeding the reactants is reversed, one will have a considerable increase of the quantity of $CN^-$ ions in the solution at the end of the reaction. In fact, when one compares the results of Example 1 with those of this example, it is seen that the quantity of $CN^-$ ions has increased from $3.24 \times 10^{-3}$ to $15.1 \times 10^{-3}$ moles, i.e., an increase of about 500%.

EXAMPLE 6

Comparative Example Illustrating the Prior Art

Into a 2000 ml glass reactor fitted with a heating bath, a thermometer, a stirrer, a reflux cooler and drawing pipe for the bubbling of nitrogen, there were introduced: 136.13 g (1.0 mole) of 3,4-dicyano-1,2,5-thiadiazole (II) and a solution obtained by dissolving 200 g of KOH at 85% titer (3.0 moles) in 1600 ml (88.83 moles) of water. As soon as stirring was commenced there occured a slightly exothermic reaction which caused the temperature to rise to 30° C. Nitrogen was caused to bubble through the solution and the whole was heated at a slow reflux for 30 minutes and then at a faster reflux for about 2 hours, bubbling through it a greater quantity of nitrogen. During this phase the evaporated water was replaced, so as to keep the level of the solution constant. The solution was then concentrated to reduce the reaction volume down to about half. It was then decolorized twice with decolorizing carbon and was partially neutralized with 187.2 ml (2.25 moles) of a solution of hydrochloric acid at 37% concentration.

The reaction mass was then cooled with an ice bath, and the precipitate was then filtered and washed with cold water repeatedly (a total of 250 ml water) and then with acetone. After drying under vacuum in an oven at 100° C. until attaining a constant weight, there were obtained 189.9 g of the monopotassium salt of the 1,2,5-thiadiazol-3,4-dicarboxylic acid (I), having a titer of 95%.

The yield, based on 3,4-dicyano-1,2,5-thiadiazole (II), amounted to 85%.

The content in $CN^-$ ions in the saponification solution, per mole of reacted 3,4-dicyano-1,2,5-thiadiazole, amounted to $16 \times 10^{-3}$ moles. This example was carried out according to the known prior art (R. N. MacDonald, W.H. Sharkey, "Journal of Polymer Science", *11* 2519 (1973). In comparison with the process of this invention, it will be noted that:

The yield of the monopotassium salt of 1,2,5-thiadiazole-3,4-dicarboxylic acid was lower.

The content in $CN^-$ ions was higher and, thus, a greater quantity of reclaiming agent is required (normally chlorine).

The consumption of KOH was greater, so that the consumption of neutralizing agent (concentrated HCl) is greater.

From the technological point of view, the prior art process is more complex than the present process inasmuch as it requires (1) a concentration step and (2) a double carbon decolorizing step of the saponification solution. For equal volumes, the productivity for the prior art process is lower than that of this process. In fact, comparing Example 1 with Example 6, it appears that the quantities of monopotassium salt at 100% purity referred to the reaction volume unity are the following:

For Example 1:

Volume — about 400 ml (21 moles of $H_2O$);
Quantity of 100% pure monopotassium salt obtained = 231.7 g. × 0.90 = 208.5 g;
Specific output: 208.5/400 = 0.52 g/ml of volume.

For Example 6:

Volume about 1600 (88.83 moles of $H_2O$);
Quantity of 100% pure monopotassium salt obtained = 189.9 g. × 0.95 = 180.4 g;
Specific output = 180.4/1600 = 0.11 g/ml of volume.

Thus, the process output for this invention is about 5 times greater than that of the prior art process.

Variations can, of course, be made without departing from the spirit and scope of the invention.

Having thus described out invention, what is desired to be secured by Letters Patent and hereby claimed is:

1. A method for preparing the monopotassium salt of 1,2,5-thiadiazol-3,4-dicarboxylic acid by double stage saponification of 3,4-dicyano-1,2,5-thiadiazole, this method comprising adding aqueous KOH to an aqueous suspension of 3,4-dicyano-1,2,5-thiadiazole in such amount that the molar ratio of 3,4-dicyano-1,2,5-thiadiazole to KOH is from about 1:1.01 to 1:0.8, and maintaining the temperature at from about 20° to 50° C. to thereby catalytically hydrogenate and form 3-cyano-4-carbamoyl-1,2,5-thiadiazole, effecting further hydrolysis by adding additional aqueous KOH in such amount as to result in an overall molar ratio of 3,4-dicyano-1,2,5-thiadiazole to KOH of from about 1:2.0 to 1:2.35 and an overall molar ratio of 3,4-dicyano-1,2,5-thiadiazole to $H_2O$ of from about 1:20 to 1:23, at a temperature of from about 85° to 100° C., to thereby form a solution of the dipotassium salt of 1,2,5-thiadaizole-3,4-dicarboxylic acid, and separating the monopotassium salt by acidifying, to a pH of from about 2 to 3, said solution of dipotassium salt of 1,2,5-thiadiazole-3,4-dicarboxylic acid.

2. The method of claim 1 wherein in the catalytic hydration step, the molar ratio of 3,4-dicyano-1,2,5-thiadiazole to KOH is from about 1:0.02 to 1:0.7.

3. The method of claim 1 wherein in the catalytic hydration step, the 3,4-dicyano-1,2,5-thiadiazole is initially suspended in about 10 moles of water.

4. The method of claim 1 wherein the catalytic hydration step is carried out by adding the aqueous KOH solution to the aqueous suspension of 3,4-dicyano-1,2,5-thiadiazole.

5. The method of claim 1 wherein the aqueous solution of 3-cyano-4-carbamoyl-1,2,5-thiadiazole which is obtained is used directly in the subsequent reaction step.

6. The method of claim 1 wherein, at the termination of the catalytic hydration step, the resulting 3-dicyano-4-carbamoyl-1,2,5-thiadiazole is separated by cooling to a temperature less than about 35° C.

7. The method of claim 1 wherein the overall molar ratios of 3,4-dicyano-1,2,5-thiadiazole/KOH/$H_2O$ are 1/2.15–2.30/21–22.

8. The method of claim 1 wherein said hydrolysis of 3-cyano-4-carbamoyl-1,2,5-thiadiazole is conducted at a temperature of from about 90° to 95° C.

9. The method of claim 1 wherein the aqueous KOH solution employed has a concentration of from about 38% to 40% by weight.

10. 3-cyano-4-carbamoyl-1,2,5-thiadiazole.

* * * * *

UNITED STATES PATENT OFFICE
CERTIFICATE OF CORRECTION

Patent No. 4,077,966  Dated March 7, 1978

Inventor(s) Giuseppe Ribaldone et al

It is certified that error appears in the above-identified patent and that said Letters Patent are hereby corrected as shown below:

Title page, line 17 of Abstract: "1,2,5-thiadiazol-3,4-diccarboxylic" should read -- 1,2,5-thiadiazole-3,4-dicarboxylic --.

Column 7, line 38: "0.22" should read -- 0.02 --.

Column 10, line 40: "out" should read -- our --.

Column 10, line 7 of claim 1: "1:1.01" should read -- 1:0.01 --.

Signed and Sealed this

Nineteenth Day of September 1978

[SEAL]

Attest:

RUTH C. MASON
Attesting Officer

DONALD W. BANNER
Commissioner of Patents and Trademarks